United States Patent
Kronberg et al.

(10) Patent No.: US 9,848,813 B2
(45) Date of Patent: Dec. 26, 2017

(54) METHOD FOR DETERMINING THE OPERATIONAL STATE OF A DRIVER

(75) Inventors: Peter Tobias Kronberg, Kärna (SE); Fredrik Sandblom, Mölndal (SE)

(73) Assignee: Volvo Lastvagnar AB, Göteborg (SE)

( * ) Notice: Subject to any disclaimer, the term of this patent is extended or adjusted under 35 U.S.C. 154(b) by 148 days.

(21) Appl. No.: 14/420,668

(22) PCT Filed: Aug. 14, 2012

(86) PCT No.: PCT/SE2012/000116
§ 371 (c)(1),
(2), (4) Date: Mar. 25, 2015

(87) PCT Pub. No.: WO2014/027933
PCT Pub. Date: Feb. 20, 2014

(65) Prior Publication Data
US 2015/0216466 A1  Aug. 6, 2015

(51) Int. Cl.
*G08B 23/00* (2006.01)
*A61B 5/18* (2006.01)
(Continued)

(52) U.S. Cl.
CPC .............. *A61B 5/18* (2013.01); *A61B 3/113* (2013.01); *A61B 5/1128* (2013.01);
(Continued)

(58) Field of Classification Search
None
See application file for complete search history.

(56) References Cited

U.S. PATENT DOCUMENTS

| 6,060,989 A * | 5/2000 | Gehlot | G08B 21/06 180/272 |
| 6,393,361 B1 * | 5/2002 | Yano | B60T 7/14 340/436 |

(Continued)

FOREIGN PATENT DOCUMENTS

EP 2564765 A1 3/2013
EP 2564766 A1 3/2013
(Continued)

OTHER PUBLICATIONS

Chinese Official Action (Jul. 5, 2016) fof corresponding Chinese App. 201280074227.X.
(Continued)

*Primary Examiner* — Julie Lieu
(74) *Attorney, Agent, or Firm* — WRB-IP LLP

(57) ABSTRACT

A method for determining an operational state of a driver of a vehicle uses an awareness detection arrangement. The awareness detection arrangement includes at least a first and a second source for generating data relating to the behavior of the driver. The method includes receiving, from the first and the second source, data relating to at least one of physiological data of the driver, the operation of the vehicle, and a model of the driver operating the vehicle, comparing the data from the first and the second source with a driver state model defining a plurality of predefined driver states for each of the first and the second source, respectively, determining based on the comparison, for each of the first and the second source, a state probability for each of the plurality of predefined driver states, and weighing the determined driver states for the first and the second source with each other for determining an overall operational state probability for the driver.

15 Claims, 4 Drawing Sheets

(51) Int. Cl.
*B60K 28/06* (2006.01)
*G08B 21/06* (2006.01)
*A61B 5/11* (2006.01)
*A61B 3/113* (2006.01)
*A61B 5/00* (2006.01)
*G06F 17/18* (2006.01)
*G08B 29/18* (2006.01)

(52) U.S. Cl.
CPC .......... *A61B 5/4809* (2013.01); *A61B 5/6893* (2013.01); *A61B 5/7264* (2013.01); *A61B 5/7275* (2013.01); *B60K 28/06* (2013.01); *G06F 17/18* (2013.01); *G08B 21/06* (2013.01); *A61B 5/11* (2013.01); *A61B 5/7246* (2013.01); *G08B 29/186* (2013.01); *G08B 29/188* (2013.01)

(56) References Cited

U.S. PATENT DOCUMENTS

| | | | |
|---|---|---|---|
| 2003/0097047 A1* | 5/2003 | Woltermann | A61B 5/165 600/300 |
| 2003/0146841 A1 | 8/2003 | Koenig | |
| 2003/0151516 A1* | 8/2003 | Basir | G08B 21/06 340/575 |
| 2005/0128092 A1 | 6/2005 | Bukman et al. | |
| 2009/0033501 A1* | 2/2009 | Chen | A61B 5/18 340/576 |
| 2009/0234552 A1* | 9/2009 | Takeda | B60W 30/16 701/96 |
| 2010/0033333 A1* | 2/2010 | Victor | A61B 3/113 340/576 |
| 2011/0022298 A1* | 1/2011 | Kronberg | G01C 21/3484 701/532 |
| 2012/0206252 A1 | 8/2012 | Sherony et al. | |
| 2012/0212353 A1* | 8/2012 | Fung | B60K 28/06 340/905 |
| 2013/0226408 A1* | 8/2013 | Fung | B60W 40/09 701/41 |
| 2013/0245886 A1* | 9/2013 | Fung | B60K 28/06 701/36 |
| 2016/0159217 A1* | 6/2016 | Kim | G08B 21/06 340/575 |

FOREIGN PATENT DOCUMENTS

| | | |
|---|---|---|
| WO | 0233529 A2 | 4/2002 |
| WO | 2008126071 A1 | 4/2008 |
| WO | 2009043650 A1 | 4/2009 |

OTHER PUBLICATIONS

International Search Report (Jun. 4, 2013) for corresponding International App. PCT/SE2012/000116.

International Preliminary Report on Patentability (Jul. 21, 2014) for corresponding International App. PCT/SE2012/000116.

European Search Report (Feb. 25, 2016) for corresponding European App. EP12 88 9739.

Yang G et al: "A driver fatigue 1-15 recognition model based on information fusion and dynamic Bayesian network", Information Sciences, Amsterdam, NL, vol. 180, No. 10, May 15, 2010(May 15, 2010), pp. 1942-1954.

Sandblom, Fredrik, Filtering and modelling for automotive safety systems, Thesis for the degree of Doctor of Philosophy, ISBN 978-91-7385-608-9, Department of Signals and Systems, Signal Processing Group Chalmers University of Technology, SE-412 90 Goteborg, Sweden (Nov. 2011).

* cited by examiner

METHOD FOR DETERMINING THE OPERATIONAL STATE OF A DRIVER

BACKGROUND AND SUMMARY

The present invention relates to improvements in relation to drowsiness detection, specifically in relation to determining the operational state of a driver operating a vehicle, by means of using a multi source input, e.g. by combining information provided by a camera and a vehicle related information source providing information relating to the operation of the vehicle.

Traffic accidents often occur due to driver impairment caused by, for example, drowsiness. In order to prevent accidents caused by driver impairment, it may be vital to provide the driver with a warning message to reestablish the attention of the driver to the surrounding traffic situation, or in a critical situation to advice the driver to take a break or switch to another driver of the vehicle.

Recently, much progress has been made in developing drowsiness detection algorithms that are based on detection of the driver's behavior, including for example using sensor arrangements for monitoring e.g. the eye closure of the driver using a camera, detecting steering wheel operational patterns, etc. By means of using more than one sensor arrangement, a redundancy may be achieved in ease one of the sensor arrangements fails to detect a drowsy driver, and accordingly an improved robustness of the drowsiness detection is made possible.

An exemplary drowsiness detection system is disclosed in US 2003/0151516 A1, where data from two different sensor arrangements are fused using intelligent software algorithms. Specifically, data is provided from a first and a second sensor arrangement, where the first sensor arrangement comprises an array of sensors mounted in the vehicle headliner and seat are used for detecting head movements, and the second sensor arrangement comprises heart rate monitoring sensors placed in the steering wheel, and used for monitoring driver characteristics indicating drowsy driver.

Even though the drowsiness defection system disclosed in US 2003/015156 A1 provides some improvements in relation to both redundancy and robustness of drowsiness detection, it fails to provide a solution suitable for more generally combining data from arbitrary sensor arrangements, possibly having different timelines and/or sampling rates of detection of driver characteristics, thereby allowing for introduction of further sensor arrangements without having to recalibrate the complete drowsiness detection system. Thus, it is therefore desirable to provide a method which allows for more flexibility in fusion of sensor data, further improving the robustness of drowsiness detection.

According to an aspect of the invention, the above is at least partly met by a method for determining an operational state of a driver of a vehicle using an awareness detection arrangement, the awareness detection arrangement comprising at least a first and a second source for generating data relating to the behavior of the driver, the method comprising receiving, from the first and the second source, data relating to at least one of physiological data of the driver, the operation of the vehicle, and a model of the driver operating the vehicle, comparing the data from the first and the second source with a driver state model defining a plurality of predefined driver states for each of the first and the second source, respectively, determining based on the comparison, for each of the first and the second source, a state probability for each of the plurality of predefined driver states, and weighing the determined driver states for the first and the second source with each other for determining an overall operational state probability for the driver.

The invention is based on the understanding that it is desirable to fuse several sources of information for making a better decision in relation to determining an operational state of a driver, but that prior art methods for fusion of information typically use optimization schemes to reach convergence for the multiple sources of information, resulting in that valuable information is lost in the process. Such optimization schemes may for example be based on the use of fixed rules to weigh the data into a single metric of driver drowsiness, neural networks, or various statistical methods to combine multiple indicators of drowsiness into a single output, which is used to issue a warning to the driver or activate certain countermeasures. A subsequent averaging or competition rule is then used to combine them into a single output. Moreover, existing solutions are often non-model based and require extensive validation.

According to the invention, physiological models of drowsiness evolution have been identified to be most useful when weighting the influence of different detectors in the final decision. Thus, it is of interest to predict the presence of a (truly) tired driver and to be able to warn in advance of a dangerous situation. The manifest drowsiness typically detected by driver state monitoring devices may be caused by both a physiological need for sleep and by fatigue caused by time-on-task or boredom. Thus, the manifest drowsiness may differ to varying degrees from the latent drowsiness actually caused by lack of sleep, in fact, there are a number of masking factors that temporarily may both increase or decrease the observed drowsiness level, such as external stimuli, long tedious road segments or even food intake. When such temporary masking factors are removed the latent drowsiness level will become dominant. In effect this may cause a person to appear fairly alert due to external stimuli, but quickly succumb to drowsiness once these masking factors are removed. Mathematical models of alertness/drowsiness can model the latent drowsiness, and when fused with the real time-monitoring of driver state, the accuracy and validity of the detection can increase significantly. Advantages includes for example improved predictive capabilities, less requirements for little customization and tuning for various implementations, resulting in a cost-effective implementation for achieving high robustness in detecting the operational state of the driver.

The inventive concept makes use of the output of multiple detectors (e.g. the first source of information, based on any sensor acting on virtually any time scale), and a predictive model of drowsiness (e.g. the second source of information and possible being a basic of a more advanced model), which is then treated using a known Bayesian approach to generate a robust multi-source indicator of drowsiness.

By means of the invention, it is possible to design for-the-purpose parameterized classes that are associated with specific actions to be triggered by separate in-vehicle systems. This means that the subsystem will be designed to carry out a critical function of these separate systems at the very core of its design, instead of trying to later define a mapping of this behavior based on a generic output of a drowsy driving detection system (e.g. based on the driver states; alert, drowsy). A specific example of this is how to design a driver state sensitive threshold that, will extend an Adaptive Cruise Control system (ACC) headway time gap for situations when the driver is drowsy. One typical way would be for the ACC system to use the output of a drowsy driving warning system, assign a specifically designed function that should determine if the measured drowsiness is significantly critical for the ACC to change its headway sensitivity or not. One would then subsequently create all necessary logic to handle potential errors or low-confidence of this data.

It should be noted that the wording "physiological data" in the following should be interpreted as all type of data that may be identified by an image based system that identifies e.g. the operator's eyes, face, body, as well as eye gaze direction, eyelid closures, or by measurement of the driver's heart rate, brain, activity, stress level, breathing, etc. Additionally, the concept of driver states and to determine such states is discussed below in relation to the detailed description of the invention.

According to an embodiment, the operational data of the driver comprises information relating to at least one of eye, face, head, arm and body motion of the operator. Such driver related, information may for example be generated by means of an image capturing device arranged within the vehicle compartment and overlooking the driver of the vehicle. Other types of sensors, generating relevant information for use in relation to the inventive concept may for example include heart rate sensors arranged in conjunction to the steering wheel or the driver seat. Additionally, movement sensors for generating indication of driver movement may be integrated within the driver seat and used for generating information useable in relation to the inventive concept.

According to a further embodiment, the operation of the vehicle may comprise information relating to at least one of time to line crossing, distance to a further vehicle travelling in front of said vehicle, steering and/or wheel operation patterns. Such vehicle related information may be generated by e.g. an image capturing device, radar equipment, or any other type of sensor used in vehicle operation.

In an embodiment, the model of the driver operating the vehicle comprises a first component relating to at least one of the time of the day and the operational time of the vehicle (e.g. time on task), and a second component relating to the drowsiness level of the driver. The second component relating to the drowsiness level of the driver is based on at least one of a model of sleep latency, time of day, time on task, a circadian rhythm, and a sleep/wake homeostatic process. An exemplary model of driver drowsiness is provided in WO09126071, by the applicant, which is incorporated by reference in its entirety.

Preferably, the outcome of inventive method, the determined state of the driver, is provided to a vehicle system configured to implement a vehicle control functionality, the vehicle system adjusting the vehicle control functionality based on the driver state. This may for example be implemented as discussed above in relation to the Adaptive Cruise Control system, and/or in relation to e.g. a forward collision warning (FCW) system as will be discussed further below in relation to the detailed description of the invention. Additionally, the determined state of the driver may be provided to a drowsy-driver detection system for generating a warning to the driver state indicate that the driver is drowsy.

According to another aspect of the invention there is provided a control system for determining an operational state of a driver of a vehicle, the control system comprising a control unit, the control unit connected to an awareness detection arrangement comprising at least a first and a second source for generating data relating to the behavior of the driver, wherein the control unit is configured to receive, from the first and the second source, data relating to at least one of physiological data of the driver, the operation of the vehicle, and a model of the driver operating the vehicle, compare the data from the first and the second source with a driver state model defining a plurality of predefined driver states for each of the first and the second source, respectively, determine based on the comparison, for each of the first and the second source, a state probability for each of the plurality of predefined driver states, and weigh the determined driver states for the first and the second source with each other for determining an overall operational state probability for the driver. This aspect of the invention, provides similar advantages as discussed above in relation to the previous aspect of the invention.

The control system may for example form pan of a vehicle system, further comprising the above disclosed awareness detection arrangement. Preferably, at least one of the first and the second source may be configured to generate operational data of the driver comprises information relating to at least one of eye, face, head, arm and body motion of the operator, where at least one of the first and the second source is an image capturing device. Additionally, at least one of the first and the second source may be configured to generate operational data of the vehicle comprises information relating to at least one of time to line crossing, distance to a further vehicle travelling in front of the vehicle, steering and/or wheel operation pattern.

According to a still further aspect of the invention, there is provided a computer readable medium embodying a computer program product for determining an operational state of a driver of a vehicle using an awareness detection arrangement, the awareness detection arrangement comprising at least a first and a second source for generating data relating to the behavior of the driver, the computer program product comprising code configured to, when executed by a processor receive, from the first and the second source, data relating to at least one of physiological data of the driver, the operation of the vehicle, and a model of the driver operating the vehicle, compare the data from the first and the second source with a driver state model defining a plurality of predefined driver states for each of the first and the second source, respectively, determine based on the comparison, for each of the first and the second source, a state probability for each of the plurality of predefined driver states, and weigh the determined driver states for the first and the second source with each other for determining an overall operational state probability for the driver. Also this aspect of the invention provides similar advantages as discussed above in relation to the previous aspects of the invention.

The processor may preferably be provided in a vehicle control unit, a computer, server or similarly, and the computer readable medium may be one of a removable nonvolatile random access memory, a hard disk drive, a floppy disk, a CD-ROM, a DVD-ROM, a USB memory, an SD memory card, or a similar computer readable medium known in the art (present and future). The present invention may be implemented using a combination of software and hardware elements.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1:
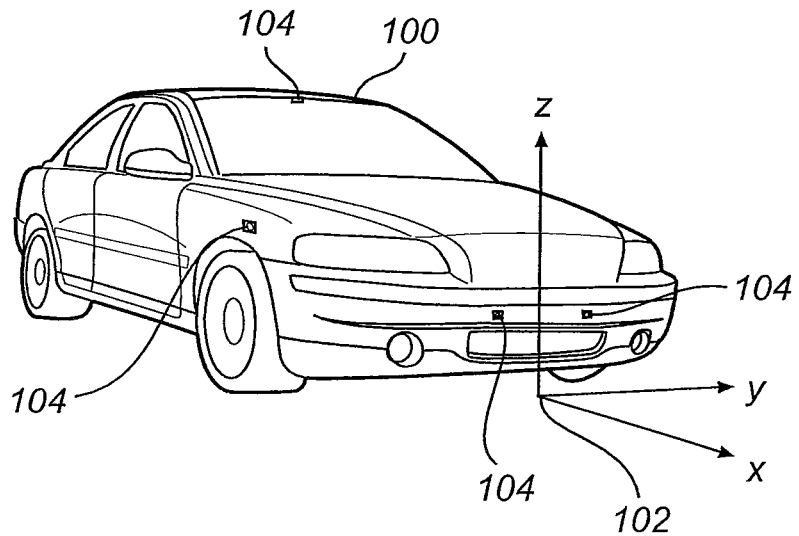
FIG. 1 is a perspective view of a vehicle equipped with external sensors and a coordinate system at its front end.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

In the following, the present invention is described with reference to a system for improving a visual input quality estimation of an operator of a vehicle. The vehicle is preferably equipped with interior sensor(s) for retrieving information of the vehicle operator and external sensor(s) for retrieving information of the vehicle operation as well as the surrounding environment of the vehicle. For the sake of better understanding, the internal and external sensors will now be described in relation to FIGS. 1-3.

FIG. 1 shows an exemplary vehicle, here illustrated as a car 100, in which a system according to the present invention may be incorporated. The car 100 is provided with external sensors 104 arranged to detect vehicle operation, such as overtaking, vehicle speed, vehicle yaw rate, etc, and objects, and zones, surrounding environment of the vehicle, e.g. lane markings, road marks, road curves, surrounding vehicles, etc. The external sensors 104 may be e.g. cameras or radar sensors. Preferably, a combination of camera and radar sensors may be used, since the camera provides a high precision when determining the height and width of the object, whereas a radar sensor provides a high precision when determining the distance to the object. Hereby, size, position, speed, etc. of the surrounding object can be determined. With reference to the position of the car 100, a coordinate system 102, here illustrated as a Cartesian coordinate system, is located at the front end of the car 100. The coordinate system 102 is arranged to follow the vehicle and the axis represent the longitudinal direction (x-axis), lateral direction (y-axis) and vertical direction (z-axis), respectively. The detected objects, in conjunction with the coordinate system 102 of the car 100, are provided to a system of the vehicle such that the system can determine the size and position of the object relative to the car 100. For example, the system may be continuously provided with object data from the different sensors 04. Hence it is also possible to determine speed and acceleration of surrounding traffic environment.

Figure 2:
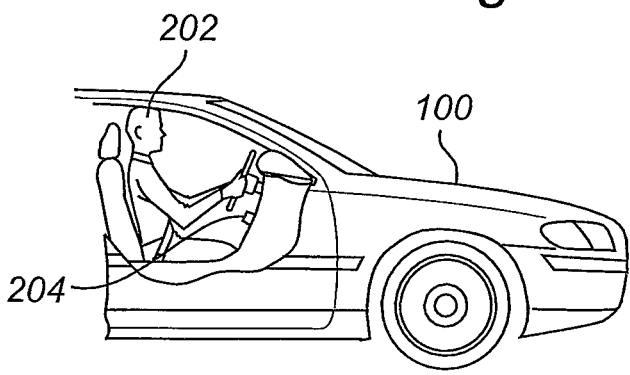
FIG. 2 is a perspective view of the interior of the vehicle, equipped with an internal sensor.

FIG. 2 illustrates an interior of a car 100 including a vehicle operator 202, wherein the vehicle 100 is equipped with an internal sensor, here illustrated as a camera system 204. The camera system 204 is arranged to measure and detect the behavior of the vehicle operator 202 during vehicle operation, and may be configured to generate an operator motion input signal indicative of physiological data comprising information relating to at least one of eye, face, head and body motion of the operator of the vehicle.

Furthermore, the camera system 204 may be arranged to focus on a predetermined number of positions of the operator's face, head, or upper body. These positions may, for example, be the eyes, eye-lids, eyebrows, nose, mouth, cheek, neck, shoulders, arms, etc. The camera system 204 may be pre-calibrated for a specific operator 202 normally operating the car or being calibrated each time an operator 202 enters the driver seat of the car 100. As the camera system 204 has detected the different positions of the operator's face or head, an estimation of facial behavior is possible for the camera system 204. The camera system 204 may hence detect, e.g. head and eye direction and movement, and derivative thereof head pose, eye saccade, combined head and eye saccade, eye closure, speed of eye closure, etc.

Figure 3:
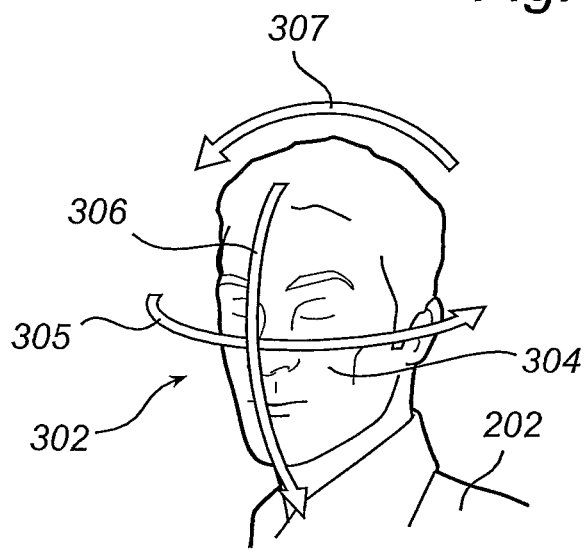
FIG. 3 illustrates a coordinate system of the face and head of a vehicle operator.

The camera system 204 may also, by use of a coordinate system 302 in connection to the operator's face 304, e.g. a operator-centric pitch/yaw coordinate system as illustrated in FIG. 3, detect if the head, or eyes, of the operator is rotating to the right or left (yaw), 305, rotating up or down (pitch), 306, or, in the case of the head movements, leaning towards the right or left shoulder (roll), 307. The coordinate system 302 of the face 304 is preferably a polar coordinate system with its origin positioned between the eyes of the operator.

Furthermore, the internal sensors may also, instead of, or additionally to the camera system 204, include other type of operator detecting means. This may, for example, include steering wheel sensors for detection of a steering behavior, sensors in the acceleration pedal and/or braking pedal for detection of inconsistent acceleration and/or braking of the car 100, sensors in various buttons of the car 100 to detect if for example, the operator 202 is adjusting any of the various functionalities of the infotainment system, etc. Further examples of internal sensors may include a breath analysis sensor or pupil size sensor for monitoring state of awareness of the operator.

For providing a further understanding of the invention, an explanation is provided below in which the concept is divided into an initial preparatory phase of parameterization and calculations of the necessary reference values, and a further usage phase of continuous detection, computation and prediction of drowsiness, including the subsequent generation of warnings to the driver or control of other vehicle functions.

In the initial preparatory phase, an expert based (e.g. off-line) parameterization of the possible driver states that characterizes the driver (drowsiness) state. From research it is known that this parameterization can be made strong and robust. The parameterization could in one embodiment be based on two states {alert, drowsy}. In another embodiment the parameterization could be based on four states {very alert, alert, drowsy, fighting sleep}.

Further states are of course possible and within the scope of the invention. As an example, taking a completely different approach, the states can be defined to correspond to the activation triggers of other vehicle functions it is meant to feed information to. The system may then either use generic functional levels or functional states tailored for a specific vehicle system. Thus, in a one embodiment, the fusion system is designed as a pre-stage to influence specific behavior of a separate vehicle system (rather than designed to be a drowsy driver detection system), implemented e.g. as a forward collision warning (FCW) system that takes driver state into account. The FCW system may then map the output of the fusion, system directly to the internal warning decision function.

Figure 4A:
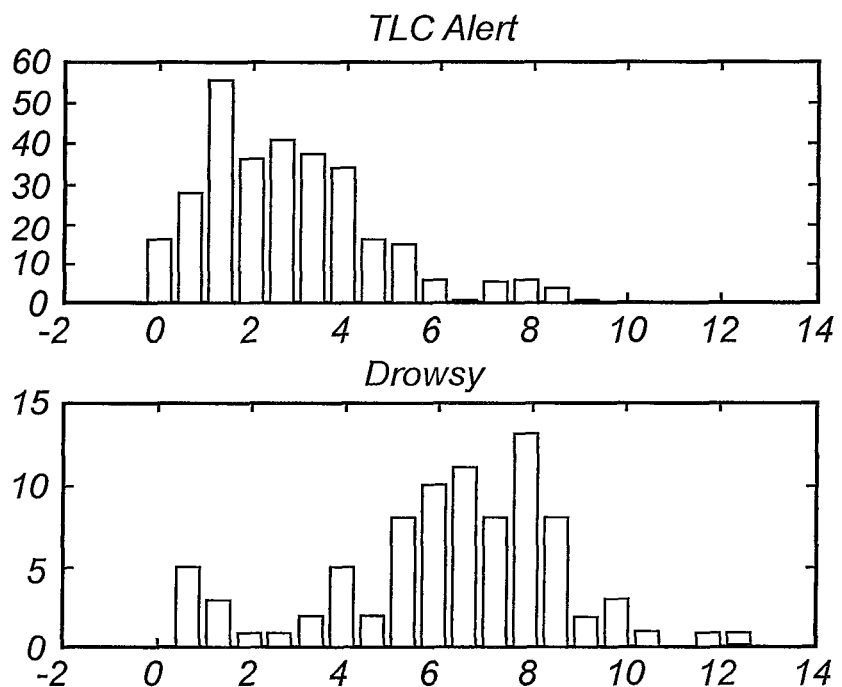
FIGS. 4a and 4b illustrate the statistical likelihood calculations of two exemplary independent indicators of the driver's state used in conjunction with the inventive method.
Figure 4B:
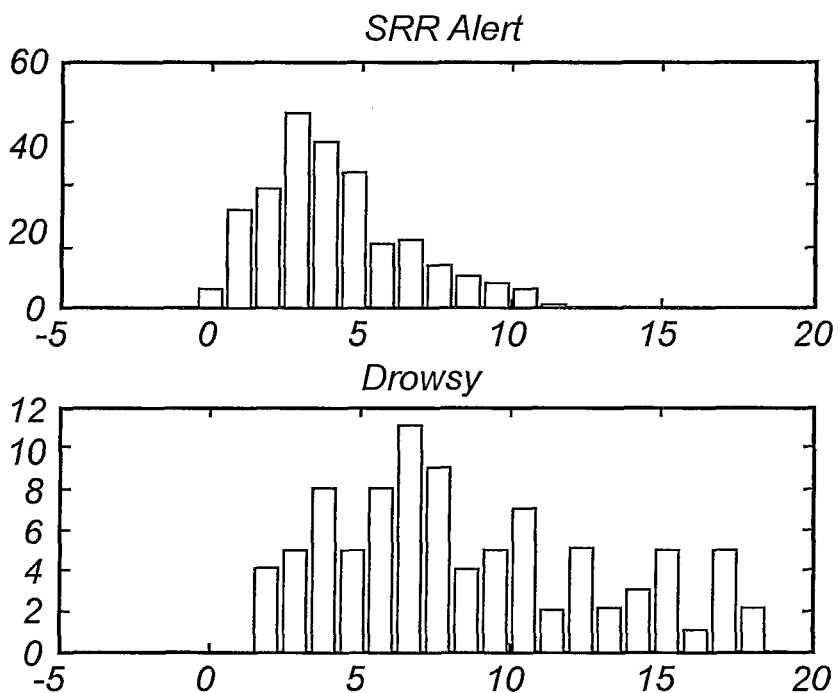

The next step in the preparatory phase involves computation of a probability mass function (pmf) of each indicator (i.e. source of information) for the defined driver states. In FIGS. 4a and b, it is illustrated the pmf for two indicators, time to line crossing (TLC) and steering wheel reversal rate (SRR), using a two state parameterization {alert, drowsy}. In practice, pre collected data of actual drowsy and alert driving may be used to create the pmfs for each indicator. Since data will always be inherently ambiguous (to some extent) there is a desire to calculate the pmf of the driver state rather than a discrete classification. In other words, the shape of the pmfs describing the indicator values are used to calculate the driver state pmf. Thus there will be several pmfs describing the distribution for the data values for each indicator, and one pmf describing the distribution between valid driver states.

Figure 5:
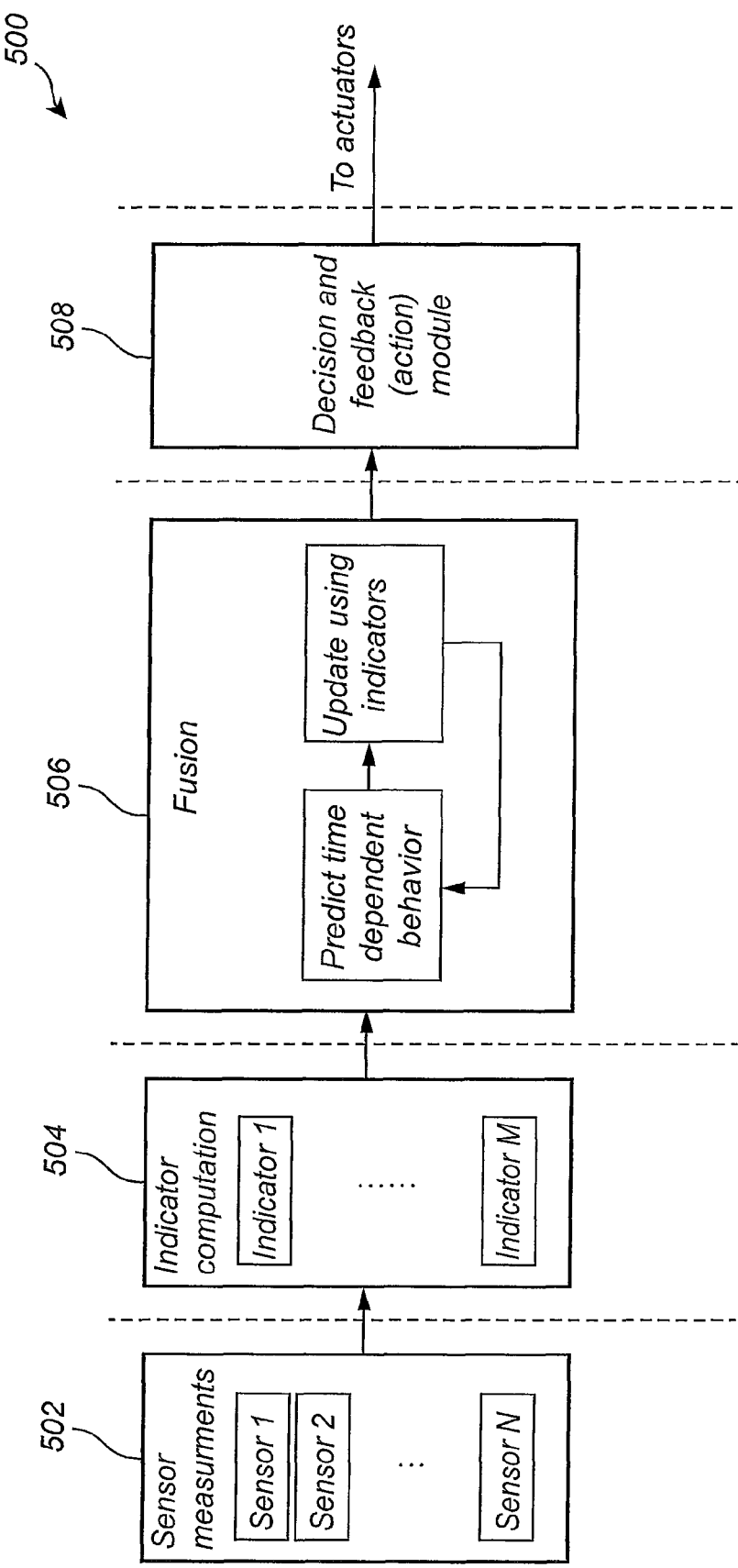
FIG. 5 conceptually illustrates a vehicle system according to a currently preferred embodiment of the invention, and FIG. 6a-c conceptually illustrates an example of the iterative adjustment of the operational state probability for the driver.

Turning now to FIG. 5, which conceptually illustrates a vehicle system 500 according to a currently preferred embodiment of the invention, for use in relation to the usage phase. The vehicle system 500 typically comprises a detection system 502 including a plurality of sensors (e.g. image capturing device(s), radar equipment, etc. as discussed above in relation to FIG. 1), an indicator computation system 504, a prediction and data fusion system 506, a decision and feedback system 508. Additionally, the vehicle system 500 typically comprises a possibility to provide a feedback to the driver of the vehicle, possibly by means of a human machine interface.

The conceptual illustration in FIG. 5 is only one of many ways of implementing the inventive concept. Additionally, the vehicle system 500 can be am asynchronously, i.e., fused estimates can be calculated at any time regardless of whether new observations have been made available. Formally, if the estimates are calculated at times $T=[t1, t2, \ldots, tN]^T$, the time difference $t2-t1$ does not necessarily equal $t3-t2$.

The drowsiness level at time $tk$ is denoted $xk$, here assumed to be a discrete variable, and the vehicle system 500 calculates its probability mass function (or probability density function if the state is assumed to be continuous). The benefit with having a discrete state vector is twofold; the state can be designed to correspond to different interventions, and the probability mass function (pmf) can be calculated exactly rather than approximated. The time stamp of the most recent indicator value used in the calculation of the pmf is shown in the notation as $p(xk|Ij)$; the conditional pmf. Data $Ij$ (bold face) denotes all indicator values accumulated up to time if. $Ij=$
  $I1, I2, \ldots Ij]$.

The operation of the vehicle system 500 may also be described using a "step-by-step" pseudo code for the indicator fusion:
  for k=1:N
  1. Store output from all connected indicators (sources of information), made available in the time interval $tk-tk-1$, $Ik=[i^1, i^2, \ldots, i^M]$, ordered by their timestamps.
  2. Update the pmf from the previous iteration, $p(xk|Ik)$, with the new data, $Ik$:
    for j=1:M
    a. Predict the drowsiness pmf to the time of the oldest indicator value, $i^j$, in $Ik$
      Calculate $p(xj|Ik-i, i^1, \ldots, i^{j-1})$.

b. Update the predicted pfm with the new indicator value, $i^j$:
    Calculate $p(xj|Ik-i, i^1, \ldots, i^j)$.
    end for
  3. Predict the pmf to the desired output time:
    Calculate $p(xk|Ik)$
  4. Apply a probabilistic decision making scheme to determine system output, e.g., warn the driver.
    end for The third step could also be used to estimate the driver state "far" in the future (e.g. 1 h) and allow for trip-planning accordingly, rather than just predict the next iteration.

The fourth step enables robust decision making since not only some estimate of drowsiness are known, but rather the whole pmf. Then any optimality criterion for interventions can be incorporated in the design.

Furthermore, the use of this approach allows a confidence value of each estimate to be computed easily.

The decision and feedback module 508 can in one embodiment take into account both, the current estimated drowsiness level and the predicted future drowsiness level (e.g. 15 minutes from now) in determining whether to issue a warning. For instance the driver may receive a warning if he is predicted to become very drowsiness within the next 15 minutes, thus giving him a chance to act proactively.

Figure 6A:
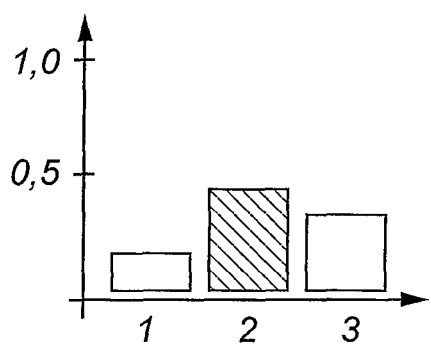
Figure 6B:
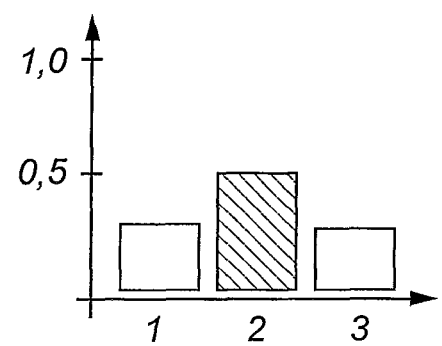
Figure 6C:
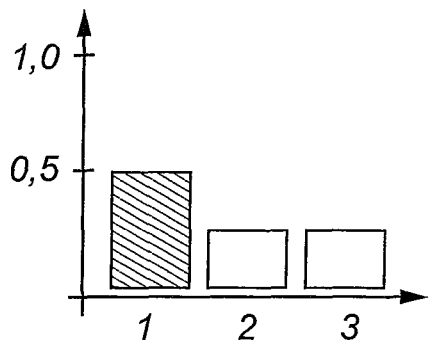

With further reference to FIGS. 6a-c where an example of the iterative adjustment of the operational state probability for a driver of a vehicle is conceptually illustrated, the driver drowsiness level x can take the values 1-3, where 1 is 'drowsy' and should yield a warning or an intervention, whereas 3 is 'alert'. Assume that the proposed system calculates that $$p(x)=[0.5, 0.1, 0.4]$$

A typical fusion system which only gives an estimate of "the best guess", would output, a '1' whereas a system that calculates the mean would give a '2'. None of these estimates contain the necessary confidence information, in this case the state is clearly ambiguous since the states 1 and 3 are almost equally likely but are naturally contradictive—the driver cannot be drowsy and alert at the same time. According to the inventive concept, this can be considered, e.g., warn if the probability $p(x=1)>0.5$ and intervene if $p(x=1)>0.9$.

In a more advanced embodiment there can be multiple actions associated with each state of the parameterization, e.g., 'Minor warning', 'Major warning', 'Intervention', 'adapting the sensitivity of auto-brake systems', 'adapting the temperature and airflow of the climate control system', 'rescheduling a delivery', etc (see table 1). To balance these actions, one cannot simply use a fusion scheme with a single output, as often proposed in existing prior art.

The iteration above may accordingly be executed when a new indicator value is available, or at times when the drowsiness estimate is needed rather than when data is made available, thereby improving the functionality of the system.

Even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. For example, the invention has mainly been described above with reference to a few embodiments. However, as is readily appreciated by the skilled addressee, other embodiments than the ones disclosed above are equally possible within the scope of the invention, as defined by the appended patent claims. For example, the invention is also applicable for trucks, buses, dumpers, wheel loaders and other type of vehicles than the above described car.

In the claims, the word "comprises" does not exclude other elements or steps, and the indefinite article "a" or "an" does not exclude a plurality. A single computer or other unit may fulfill the functions of several items recited in the claims. The mere fact that certain measures are recited in mutually different dependent claims does not indicate that a combination of these measured cannot be used to advantage.

The invention claimed is:

1. A method for determining an operational state of a driver of a vehicle using an awareness detection arrangement, the awareness detection arrangement comprising at least a first and a second source for generating data relating to the behavior of the driver, the method comprising:
   receiving, from the first and the second source, data relating to at least one of physiological data of the driver, the operation of the vehicle, and a model of the driver operating the vehicle;
   comparing the data from the first and the second source with a driver state model defining a plurality of predefined driver states for each of the first and the second source, respectively;
   determining based on the comparison, for each of the first and the second source, a state probability for each of the plurality of predefined driver states including determining one of a probability mass function for each of the plurality of predefined driver states; and
   weighing the determined driver states for the first, and the second source with each other for determining an overall operational state probability for the driver.

2. Method according to claim 1, wherein the physiological data of the driver comprises information relating to at least one of eye, face, head, arm and body motion of the operator.

3. Method according to claim 1, wherein the operation of the vehicle comprises information relating to at least one of time to line crossing, distance to a further vehicle arrange in front of the vehicle, steering and/or wheel operation pattern.

4. Method according to claim 1, wherein the model of the driver operating the vehicle comprises a first component relating to at least one of the time of the day and the operational time of the vehicle and a second component relating to the drowsiness level of the driver.

5. Method according to claim 4, wherein the second component relating to the drowsiness level of the driver is based on at least one of a model of sleep latency, time of day, time on task, a circadian rhythm, and a sleep/wake homeostatic process.

6. Method according to claim 1, wherein the plurality of predefined driver states comprises at least two states defined as drowsy and alert, respectively, preferably four states defined as very alert, alert, drowsy and fighting sleep, respectively.

7. Method according to claim 1, wherein the determined state of the driver is provided to a vehicle system configured to implement a vehicle control functionality, the vehicle system adjusting the vehicle control functionality based on the driver state.

8. Method according to claim 1, wherein the deter lined state of the driver is provided to a drowsy driver detection system for generating a warning to the driver state indicate that the driver is drowsy.

9. A control system for determining an operational state of a driver of a vehicle, the control system comprising a control unit, the control unit connected to an, awareness detection arrangement comprising at least a first and a second source for generating data relating to the behavior of the driver, wherein the control unit is configured to:
   receive, from the first and the second source, data relating to at least one of physiological data of the driver, the operation of the vehicle, and a model of the driver operating the vehicle;
   compare the data from the first and the second source with a driver state model defining a plurality of predefined driver states for each of the first and the second source, respectively;
   determine based on the comparison, for each of the first and the second source, a state probability for each of the plurality of predefined driver states including determining one of a probability mass function for each of the plurality of predefined driver states; and
   weigh the determined driver states for the first and the second source with each other for determining air overall operational state probability for the driver.

10. Control system according to claim 9, wherein the control unit is further configure to provide the determined state of the driver to a vehicle system configured to implement a vehicle control functionality, the vehicle system adjusting the vehicle control functionality based on the driver state.

11. A vehicle system, comprising
   a control system for determining an operational state of a driver of a vehicle, and
   an awareness detection arrangement,
   the control system comprising a control unit, the control unit being connected to the awareness detection arrangement,
   the awareness detection arrangement comprising at east a first and a second source for generating data relating to the behavior of the driver,
   wherein the control unit is configured to:
      receive, from the first and the second source, data relating to at least one of physiological data of the driver, the operation of the vehicle, and a model of the driver operating the vehicle;
      compare the data from the first and the second source with a driver state model defining a plurality of predefined driver states for each of the first and the second source, respectively;
      determine based on the comparison, for each of the first and the second source, a state probability for each of the plurality of predefined driver states including determining one of a probability mass function for each of the plurality of predefined driver states; and
      weigh the determined driver states for the first and the second source with each other for determining an overall operational state probability for the driver.

12. Vehicle system according to claim 11, wherein at least one of the first and the second source is configured to generate physiological data of the driver comprising information relating to at least one of eye, face, head, arm and body motion of the operator.

13. Vehicle system according to claim 11, wherein at least one of the first and the second source is an image capturing device.

14. Vehicle system according to claim 11, wherein at least one of the first and the second source is configured to generate operational data of the vehicle comprising information relating to at least one of time to line crossing, distance to a further vehicle arrange in front of the vehicle, steering and/or wheel operation pattern.

15. A non-transitory computer readable medium embodying a computer program product for determining an operational state of a driver of a vehicle using an awareness detection arrangement, the awareness detection arrangement comprising at least a first and a second source for generating data relating to the behavior of the driver, the computer program product comprising code configured to, when executed by a processor:
- receive, from the first and the second source, data relating to at least one of physiological data of the driver, the operation of the vehicle, and a model of the driver operating the vehicle;
- compare the data from the first and the second source with a driver state model defining a plurality of predefined driver states for each of the first and the second source, respectively;
- determine based on the comparison, for each of the first and the second source, a state probability for each of the plurality of predefined driver states including determining one of a probability mass function for each of the plurality of predefined driver states; and
- weigh the determined driver states for the first and the second source with each other for determining an overall operational state probability for the driver.

* * * * *